United States Patent
Gvodas, Jr.

(10) Patent No.: US 10,328,184 B2
(45) Date of Patent: Jun. 25, 2019

(54) WOUND TREATMENT DEVICE

(71) Applicant: John M Gvodas, Jr., Schwenksville, PA (US)

(72) Inventor: John M Gvodas, Jr., Schwenksville, PA (US)

(*) Notice: Subject to any disclaimer, the term of this patent is extended or adjusted under 35 U.S.C. 154(b) by 0 days.

(21) Appl. No.: 13/870,070

(22) Filed: Apr. 25, 2013

(65) Prior Publication Data

US 2013/0303975 A1 Nov. 14, 2013

Related U.S. Application Data

(60) Provisional application No. 61/644,052, filed on May 8, 2012.

(51) Int. Cl.
*A61M 35/00* (2006.01)
*A61M 1/00* (2006.01)
*A61M 13/00* (2006.01)

(52) U.S. Cl.
CPC .......... *A61M 1/0031* (2013.01); *A61M 13/00* (2013.01); *A61M 35/00* (2013.01); *A61M 1/0037* (2013.01); *A61M 1/0084* (2013.01); *A61M 1/0088* (2013.01); *A61M 13/003* (2013.01); *A61M 2202/0208* (2013.01)

(58) Field of Classification Search
CPC ..... A61F 13/00; A61F 13/00068; A61M 1/00; A61M 1/0023; A61M 1/0031; A61M 25/00; A61M 27/00; A61M 27/002
USPC ........ 601/1, 6, 9, 10, 11; 602/41–43, 52–53, 602/78
See application file for complete search history.

(56) References Cited

U.S. PATENT DOCUMENTS

| | | | |
|---|---|---|---|
| 4,971,609 A | 11/1990 | Pawlos | |
| 6,432,077 B1 * | 8/2002 | Stenzler | A61M 1/0088 604/23 |
| 7,429,252 B2 | 9/2008 | Sarangapani | |
| 7,534,240 B1 | 5/2009 | Johnson | |
| 2006/0116620 A1 * | 6/2006 | Oyaski | A61M 1/0084 602/41 |
| 2006/0230931 A1 * | 10/2006 | Bliss et al. | 95/130 |
| 2010/0298792 A1 * | 11/2010 | Weston et al. | 604/319 |
| 2012/0116334 A1 * | 5/2012 | Albert | A61F 13/02 604/319 |

OTHER PUBLICATIONS

Kalypto Medical—Brochure1 (2 pages).
Kalypto Medical Brochure2 (4 pages).
Kalypto Medical—Case Study (1 page).
TransCu O2 System Overview (2 pages).
O2 NPWT Combo—Concept (3 pages).

* cited by examiner

Primary Examiner — Kim M Lewis
(74) Attorney, Agent, or Firm — Gearhart Law, LLC

(57) ABSTRACT

The current invention discloses a wound treatment device having a wound covering member, an applicator unit, and two lumens. The wound covering member may cover a wound. Sealing mechanism of the wound covering member may be used to form a sealed wound enclosure over and around the wound. The two lumens, including a negative pressure lumen and an oxygen lumen, connect the wound enclosure to the applicator unit. The applicator may be used to apply alternating and cycling negative pressure and oxygen to the wound enclosure, facilitating the wound healing process. The levels and durations of negative pressure, as well as the purity, amount, and durations of oxygen, may be adjusted by the applicator unit.

7 Claims, 1 Drawing Sheet

WOUND TREATMENT DEVICE

CLAIM OF PRIORITY

This application is a U.S. utility application claiming priority to U.S. provisional application 61/644,052, the contents of which are fully incorporated herein.

FIELD OF THE INVENTION

The current invention relates to a wound treatment device and related methods. In particular, the current invention relates to a device that may be used to treat a wound by applying repeated cycles of intermittent negative pressure and oxygen.

BACKGROUND OF THE INVENTION

Wound treatment is a crucial part of healthcare. Various methods and devices have been developed to improve the quality of care that may be provided in wound treatment and the healing process. Among these approaches are the application of negative pressure and use of oxygen.

Negative pressure wound treatment (NPWT), the process of applying a vacuum to a wound, is an accepted and established modality of treating a variety of wound types. The devices on the market today principally include four components: a mechanical suction pump, a dressing (foam or gauze) which interfaces with the wound bed, a cover dressing to create a seal over the wound, and an exudate collection canister. The pumps for these NPWT systems come in a variety of shapes and sizes, as do the dressing kits and canisters. However, all NPWT systems do the same fundamental thing: create a vacuum or "negative pressure" environment at the wound site, while simultaneously extracting/sucking the exudate from the wound.

In addition, the used of oxygen in wound healing is also an accepted and established modality of treating a variety of wound types. However, the manner by which oxygen is delivered to the wound site varies greatly. Modalities for delivering oxygen to the wound site range from: full body hyperbaric chambers, to segmental (limb) hyperbaric chambers, to electro chemical dressing kits, to portable/wearable oxygen generating devices which use fuel cell technology to deliver micro doses of pure oxygen to the wound site under the dressing cover.

The benefits of the negative pressure treatment include, among others, improving blood flow to the wound site and flattening the wound bed to facilitate healing. On the other hand, applying oxygen to the wound site helps to improve cell metabolism and regeneration, thus enhancing the capacity to heal. These two approaches utilize non-overlapping mechanisms and may have combined effects that are more significant than each one alone. The current invention discloses a device and related methods to apply negative pressure and oxygen to the wounds in an alternating and cycling manner, further improving the wound healing process.

In summary, various devices are known in the art, but their structures are distinctively different from the current invention. Moreover, the other inventions fail to address all of the problems solved by the invention described herein. One embodiment of this invention is illustrated in the accompanying drawings and will be described in more detail herein below.

SUMMARY OF THE INVENTION

The current invention discloses a wound treatment device, comprising: a wound covering member having an inner side and an outer side, wherein the wound covering member covers a wound and the inner side faces the wound, there is a sealing mechanism on the inner side of the wound treating pad, and the sealing mechanism encircles the wound, attaches to skin surrounding the wound, and defines a sealed wound enclosure; a negative pressure lumen connected to the outer side of the wound treating pad; a negative pressure pump connected to the negative pressure lumen, the negative pressure pump being capable of applying intermittent negative pressure to the wound enclosure; an oxygen lumen connected to the outer side of the wound treating pad; and an oxygen delivery device connected to the oxygen tube, the oxygen deliver delivery being capable of delivering intermittent oxygen to the wound enclosure.

Using the device described above, the user of the device may alternate the application of negative pressure and oxygen to the wound bed, allowing faster and more complete recovery. The wound treatment device may further comprise a control mechanism connected to the pump and the oxygen delivery system, the control mechanism may be used to initiate, adjust, and end the application of negative pressure and the delivery of oxygen. With the control mechanism, the user of the wound treatment device may easily control the treatment process and change the durations, cycles, and intensity of the treatments.

Preferably, the negative pressure pump, the oxygen delivery device, and the control mechanism are integrated into a single applicator unit. The applicator unit is preferred to be small in scale, light, and portable. Since the applicator unit is likely to be the heavy part of the wound treatment device, such a design allows the device to be carried around by the patient, enabling the patient to stay mobile while receiving treatment. Additional benefits may also be conferred by the device disclosed herein. For example, the negative pressure lumen may be used to collect the exudate from the wound.

In addition to the device described above, the current invention also discloses a method to treat a wound, comprising: covering the wound with a wound covering member and forming a sealed wound enclosure over and around the wound; applying repeated cycles of wound treatment, wherein each cycle of wound treatment comprises: applying negative pressure to the wound enclosure for a first duration, and delivering oxygen to the wound enclosure for a second duration.

According to the wound to be treated, the user of the device may adjust the durations for applying the negative pressure and oxygen. For example, the user may set the first duration to be 30 minutes and the second duration to be 29 seconds.

Similarly, other parameters of the treatment may also be adjusted. For example, the level of negative pressure may be changed in a certain range. In addition, the purity of the oxygen and the amount of oxygen delivered may also be adjusted.

In general, the present invention succeeds in conferring the following, and others not mentioned, desirable and useful benefits and objectives.

It is an object of the present invention to provide a wound treatment device that may be used to facilitate the healing of wounds on humans and other subjects.

It is an object of the present invention to provide a wound treatment device that forms a sealed enclosure over and around the wound.

It is an object of the present invention to provide a wound treatment device that applies negative pressure and oxygen to a wound site in alternate and cycling manner.

It is an object of the present invention to provide a wound treatment device that is light and portable.

It is another object of the current invention to provide a wound treatment device that may be used for different kinds of wounds.

It is another object of the current invention to provide a wound treatment device that may be used for wounds on different parts of a body.

It is still another object of the current invention to provide a wound treatment device that is easily adjustable.

It is another object of the current invention to provide a wound treatment device that allows adjustment for the level of negative pressure.

It is yet another object of the current invention to provide a wound treatment device that allows adjustment of oxygen purity and amount.

It is another object of the current invention to provide a wound treatment device that uses pre-set programs for application of negative pressure and oxygen.

It is yet another object of the current invention to provide a wound treatment device that is easy to use and easy to manufacture.

DESCRIPTION OF THE PREFERRED EMBODIMENTS

Figure 1:
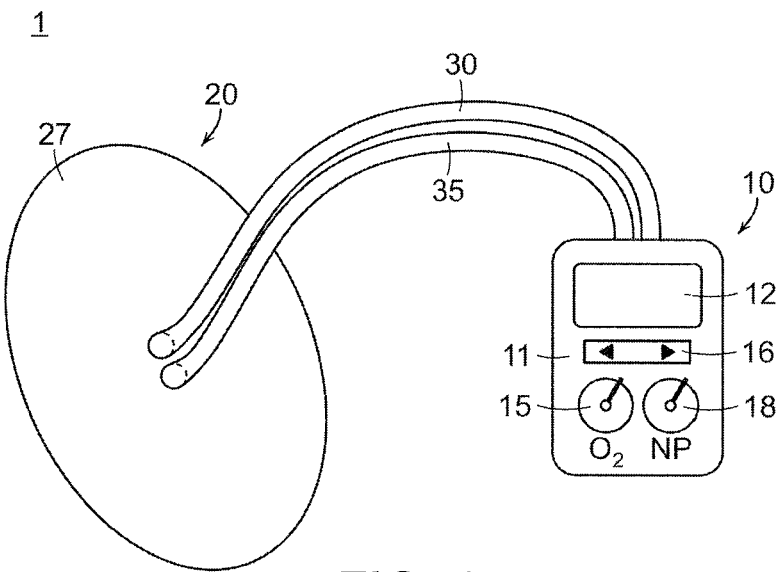
FIG. 1 shows a top perspective view of a wound treatment device.

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

FIG. 1 shows a top perspective view of a wound treatment device 1. Shown in FIG. 1 is the wound treatment device 1 having an applicator unit 10 and a wound covering member 20. The wound covering member 20 has an outer side 27 and an inner side 25 (not shown in FIG. 1). The applicator unit 10 has a pump body 11, a display 12, a negative pressure adjuster 18, an oxygen adjuster 15, and a program control 16. The applicator unit 10 is connected to the wound covering member 20 with two lumens: a negative pressure lumen 30 and an oxygen lumen 35. The negative pressure lumen 30 and the oxygen lumen 35 are connected to the outer side 27 of the wound covering member 20.

Figure 2:
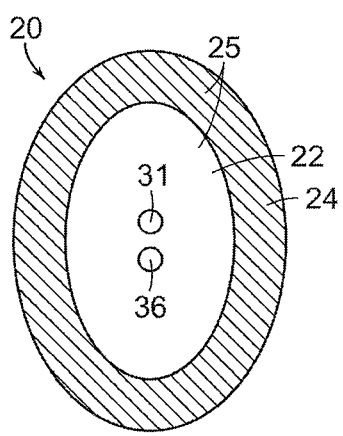
FIG. 2 shows a bottom view of a wound covering member.

FIG. 2 shows a bottom view of a wound covering member 20. Shown is the inner side 25 of the wound covering member 20. There is a sealing circle 24 on the inner side 25 of the wound covering member 20. Within the sealing circle 24 is a central area 22. Shown in FIG. 2 are also a negative pressure aperture 31 and an oxygen aperture 36.

Figure 3:
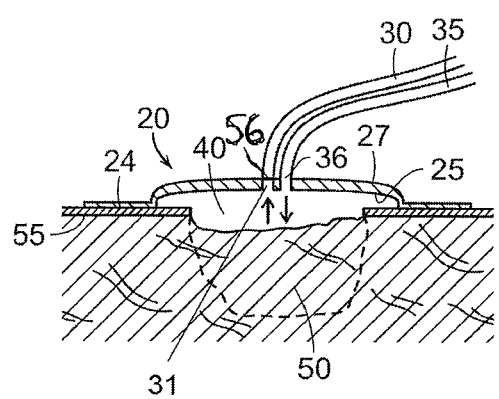
FIG. 3 shows a sectional view of a wound site that is covered by the wound covering member.

FIG. 3 shows a sectional view of a wound site that is covered by the wound covering member 20. Shown in FIG. 3 is a wound 50 surrounded by skins 55. The wound covering member 20 covers the wound 50 and the inner side 25 faces the wound 50 and the outer side 27 faces away from the wound 50. The sealing circle 24 attaches to skins 55 surrounding the wound 50, forming a sealed wound enclosure 40 over and around the wound 50. The negative pressure lumen 30 and oxygen lumen 35 connect directly to the wound covering member 20. Through the negative pressure aperture 31, negative pressure may be applied to the wound enclosure 40. Similarly, oxygen may be delivered to the wound enclosure 40 through the oxygen aperture 36.

To ensure effective application of negative pressure and oxygen to the wound bed, a sealing must be formed over and around the wound. Therefore, a wound covering member 20 is included in the current invention. There are multiple wound covering designs available on the market and such designs may be utilized by the current invention. The available wound covering designs include but are not limited to: Kalypto® dressings, Venturi™ sealing kits, and Chariker-Jeter™ sealing kits. Alternatively, the current invention may introduce novel wound covering mechanisms that include new and improved features.

Referring to FIG. 1 and FIG. 2, in general, the wound covering member 20 has an inner side 25 and an outer side 27. The inner side is defined as the side of the wound covering member 20 that faces the wound when the wound covering member 20 is attached. The inner side 25 of the wound covering member 20 may have a sealing circle 24 and a central area 22. Referring to FIG. 3, when the wound covering member 20 is applied, the sealing circle 24, which is preferred to be sticky, attaches to the skins 55 around the wound 50, forming a wound enclosure 40 over and around the wound 50. However, it should be noted that the specific design of the wound covering member 20 may be altered. As long as the basic requirement of forming a seal over and around the wound may be accomplished, any kinds of design for the wound covering member 20 are acceptable.

To apply negative pressure and oxygen, two lumens are needed. In the embodiment shown in FIG. 1 and FIG. 3, the wound treatment device 1 includes a negative pressure lumen 30 and an oxygen lumen 35. The negative pressure lumen 30 and the oxygen lumen 35 may be structurally separated, making it easier to clean and replace each lumen. Alternatively, the negative pressure lumen 30 and the oxygen lumen 35 may be restrictively positioned in parallel or may be two lumens included in a single tube, allowing easier placement and connection.

The applicator unit 10 shown in FIG. 1 may provide the power for applying the negative pressure and the oxygen. The negative pressure may be produced by a negative pressure pump; the oxygen may be delivered by an oxygen delivery device; and the wound treatment process may be controlled by a control mechanism. The negative pressure pump, the oxygen delivery device, and the control mechanism may be three or two separate structures. For example, the oxygen delivery device may also be a pump that may be combined with the negative pressure pump. FIG. 1 shows the preferred embodiment, wherein the negative pressure pump, the oxygen delivery device, and the control mechanism are integrated into a single applicator unit 10.

Referring to FIG. 1, the applicator unit 10 has a pump body 11, a display 12, a negative pressure adjuster 18, an oxygen adjuster 15, and a program control 16. Here the oxygen adjuster 15 controls the delivery of oxygen; the negative pressure adjuster 18 controls and the application of negative pressure, and the program control 16 may be used for input of specific treatment cycles and programs, allowing easy modification and control. Nevertheless, it should be clear that the design of the applicator unit 10 may be altered according to the specific requirements of the wounds to be treated, the level of negative pressure and oxygen to be applied, and the convenience and aesthetic preference of the user. For example, the applicator unit 10 may an integration of a TransCu $O_2$™ pump for oxygen diffusion and a Kalypto™ Medical negative pressure pump.

Referring to FIG. 2 and FIG. 3, the negative pressure lumen 30 and the oxygen lumen 35 are linked to the sealed wound enclosure 40 and they use the negative pressure aperture 31 and oxygen aperture 36 as inlet/outlet for the application of negative pressure and oxygen. Suctions from the applicator unit 10 through the negative pressure lumen 30 and negative pressure aperture 31 apply negative pressure to the wound enclosure 40, facilitating wound healing. In addition, the exudate from the wound may be removed by suction through the negative pressure lumen 30. In that case, the applicator unit 10 may include an exudate chamber for the collection of the exudate. Alternatively, there may be absorbent material stuffed at the central area 22 for the absorption of the exudate, making it necessary to periodically change the absorbent material to clean up the wound bed. To ensure clear suction, a valve 56 may be installed at the negative pressure aperture 31. Oxygen may be delivered to the wound enclosure 40 from the applicator unit 10 through the oxygen lumen 35 and oxygen aperture 36. The applicator unit 10 may include an oxygen generating device such as the Focus™ portable oxygen concentrator, or other approaches capable of providing high purity oxygen. Alternatively, the applicator unit 10 may simply provide a delivery mechanism, such as a pump, to delivery oxygen stored in a separate container, such as a carbon fiber M-6 cylinder with a meter dose capable regulator.

The negative pressure applied to the wound enclosure 40 may range from 10 mm/hg to 300 mm/hg, with a preferred ranged of 40 to 160 mm/hg. The purity of oxygen may range from 50% to 100%, with the preferred range of 84-100%. The amount of oxygen delivered generally ranges from 1 to 100 ml, with the preferred range of 2 to 10 ml.

Using the wound treatment device 1, a patient or a caregiver may control the patient's treatment process. Under the instructions of a medical professional, a treatment cycle may be developed for optimization of healing results. The treatment cycle and other parameters may be programmed into the applicator unit 10 and simple instructions may initiate, adjust, pause, and stop the program.

Generally, a treatment process includes a plurality of treatment cycles, wherein each treatment cycle includes alternate application of negative pressure and oxygen. In particular, the current invention teaches a method to treat a wound 50, comprising: covering the wound 55 with a wound covering member 20 and forming a sealed wound enclosure 40 over and around the wound 50; applying repeated cycles of wound treatment, wherein each cycle of wound treatment comprises: applying negative pressure to the wound enclosure 40 for a first duration, and delivering oxygen to the wound enclosure 40 for a second duration. The first duration and second duration may vary in length and may be adjusted according to the wound to be treated, the body part the wound is on, the physical conditions of the patients, the parameters for the negative pressure and oxygen, and other related elements.

More particularly, the treatment may include multiple repeated cycles and each cycle may conform to the steps shown in Table 1.

TABLE 1

| Time Interval | Action taken |
| --- | --- |
| START | Delivers suction to sealed wound enclosure |
| 30 minutes later | Releases suction |
| 30 seconds later | Maintain the decreased pressure state. |
| 31 seconds later | Delivers a single bolus of $O_2$. |
| 29 seconds later | Delivers suction to desired negative pressure setting |

As indicated above, the durations and other parameters of the treatment may be altered for optimized results.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A wound treatment device, comprising:
   a wound covering member having an inner surface and an outer surface with a first aperture and a second aperture disposed in a central portion of the wound covering member,
      wherein the wound covering member is configured to cover a wound and the inner surface is configured to face the wound,
      there is a sealing mechanism on the inner surface of the wound covering member, and the sealing mechanism is configured to encircle the wound, forming an uninterrupted seal with a periphery of the wound, thereby defining a sealed wound enclosure;
   a negative pressure lumen directly attached to the outer surface of the wound covering member at the first aperture,
      wherein the negative pressure lumen has a valve disposed at the first aperture;
   a negative pressure pump connected to the negative pressure lumen, the pump being capable of applying intermittent negative pressure to the wound enclosure;
   an oxygen lumen directly attached to the outer surface of the wound covering member at the second aperture;
   an oxygen delivery device connected to the oxygen lumen, the oxygen delivery device being capable of delivering intermittent oxygen to the wound enclosure; and
   an oxygen adjuster being capable of adjusting the purity and amount of oxygen;
   wherein the negative pressure lumen and the oxygen lumen wholly reside at or above the inner surface of the sealed wound enclosure.

2. The wound treatment device of claim 1, further comprising a control mechanism connected to the negative pressure pump and the oxygen delivery device, the control mechanism controls the application of negative pressure and the purity and amount of the oxygen delivered.

3. The wound treatment device of claim 1, wherein the negative pressure pump, the oxygen delivery device, and the control mechanism are integrated into a single applicator unit.

4. A method to treat a wound, comprising:
   covering the wound with a wound treatment device of claim 1 and forming a sealed wound enclosure having an uninterrupted seal over and around the wound;
   applying repeated cycles of wound treatment, wherein each cycle of wound treatment consists of:

applying a negative pressure of about 40 mmHg to about 160 mmHg to the wound enclosure for a first duration, and subsequently releasing the negative pressure and delivering oxygen having a purity of about 84% to about 100% to the wound enclosure for a second duration.

5. The method to treat a wound as claim 4, wherein the first duration is 30 minutes.

6. The method to treat a wound as claim 4, wherein the second duration is 29 seconds.

7. The method to treat a wound as claim 4, wherein about 2 mL to about 10 mL of oxygen are delivered to the wound enclosure.

* * * * *